United States Patent
Hoshino et al.

(10) Patent No.: US 6,984,510 B2
(45) Date of Patent: Jan. 10, 2006

(54) VITAMIN $B_6$-PHOSPHATE PHOSPHATASE

(75) Inventors: Tatsuo Hoshino, Kamakura (JP); Keiko Ichikawa, Fujisawa (JP); Masaaki Tazoe, Yokohama (JP)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/481,099

(22) PCT Filed: Jun. 14, 2002

(86) PCT No.: PCT/EP02/06625

§ 371 (c)(1),
(2), (4) Date: Dec. 17, 2003

(87) PCT Pub. No.: WO03/000875

PCT Pub. Date: Jan. 3, 2003

(65) Prior Publication Data

US 2004/0176596 A1    Sep. 9, 2004

(30) Foreign Application Priority Data

Jun. 20, 2001    (EP) .................................. 01114915

(51) Int. Cl.
  *C12N 9/12*   (2006.01)
  *C12N 9/00*   (2006.01)
  *C12P 17/00*  (2006.01)
  *C12P 1/00*   (2006.01)

(52) U.S. Cl. ...................... 435/194; 435/193; 435/183; 435/117; 435/41

(58) Field of Classification Search ................ 435/117, 435/41, 183, 194, 193
See application file for complete search history.

(56) References Cited

U.S. PATENT DOCUMENTS 5,766,894 A * 6/1998 Hoshino et al. ............ 435/122

FOREIGN PATENT DOCUMENTS

EP    0 950 715    10/1999

OTHER PUBLICATIONS

Costello, R.B., ed. 1991. Webster's College Dictionary, Random House. p. 893.*
Domenech, C. 1996. Purification and preliminary characterization of Rhizobium meliloti acid phosphatase. Int. J. Bio-Chromatography 2: 1-8.*
Love, S.H. 1956. Synthesis of purine intermediates by a cell-free extract of Escherichia coli. J. Bacteriol. 72: 628-631.*
Lucchini, A.E., et al. 1990. Choline derivatives increase two different acid phosphatases in Rhizobium meliloti and Pseudomonas aeruginosa. Arch. Microbiol. 153: 596-599.*
Tazoe, M., et al., "Biosynthesis of Vitamin $B_6$ Rhizobium," The Journal of Biological Chemistry, vol. 275 (15) 11300-305 (2000).
Fonda, M., "Purification and Characterization of Vitamin $B_6$-Phosphate Phosphatase from Human Erythrocytes," The Journal of Biological Chemistry vol. 267 (22) 15978-983 (1992).

* cited by examiner

Primary Examiner—Sandra E Saucier
Assistant Examiner—Lora E Barnhart
(74) Attorney, Agent, or Firm—Bryan Cave LLP

(57) ABSTRACT

A purified vitamin $B_6$-phosphate phosphatase (VB6PP), having the following physico-chemical properties: a) Molecular weight: 29,000±5,000 (consisting of a monomer having a molecular weight of 29,000±5,000); b) Co-factor: $Mn^{2+}$, $Mg^{2+}$, $Co^{2+}$, $Sn^{2+}$, or $Ni^{2+}$; c) Substrate specificity: active on pyridoxol 5'-phosphate, pyridoxal 5'-phosphate and pyridoxamine 5'-phosphate; d) Optimum temperature: 30–400° C. at pH 7.5; and e) Optimum pH: 7.0–8.0 is disclosed. Also disclosed are a process for producing VB6PP from a microorganism belonging to the genus *Sinorhizobium* capable of producing VB6PP, a process for producing vitamin $B_6$ from vitamin $B_6$-phosphate (VB6P) utilizing VB6PP, and a cell-free extract of a microorganism belonging to the genus *Sinorhizobium* capable of producing VB6PP.

19 Claims, No Drawings

VITAMIN B$_6$-PHOSPHATE PHOSPHATASE

This application is the National Stage of International Application No. PCT/EP02/06625, filed Jun. 14, 2002.

The present invention relates to a novel enzyme, namely vitamin B$_6$-phosphate phosphatase (hereinafter referred to as VB6PP), a process for producing VB6PP and a process for producing vitamin B$_6$ from vitamin B$_6$-phosphate (hereinafter referred to as VB6P) utilizing VB6PP and a cell-free extract of a specific microorganism capable of producing VB6PP.

"Vitamin B$_6$" as used in the present invention includes pyridoxol, pyridoxal and pyridoxamine. Vitamin B$_6$ is one of the important vitamins for the nutrition of human, animals, plants and microorganisms.

It is well-known that nonspecific phosphomonoesterases such as alkaline and acid phosphatases hydrolyze various kinds of phosphoric acid-monoester compounds including VB6P to the corresponding ester-free compounds [Glenn and Dilworth, Arch. Microbiol. 126:251–256 (1980)]. There is no report on VB6P-specific phosphatase except for a phosphatase purified from human erythrocytes [Fonda, J. Biol. Chem. 267:15978–15983 (1992)].

It is an object of the present invention to provide the novel VB6PP which acts on VB6P to produce vitamin B$_6$. The VB6PP of the present invention has the following physico-chemical properties:

a) Molecular weight: 29,000±5,000 (consisting of a monomer having a molecular weight of 29,000±5,000)
b) Co-factor: $Mn^{2+}$, $Mg^{2+}$, $Co^{2+}$, $Sn^{2+}$ or $Ni^{2+}$
c) Substrate specificity: active on pyridoxol 5'-phosphate (hereafter referred to as PNP), pyridoxal 5'-phosphate (hereafter referred to as PLP) and pyridoxamine 5'-phosphate (hereafter referred to as PMP)
d) Optimum temperature: 30–40° C. at pH 7.5
e) Optimum pH: 7.0–8.0.

It is another object of the present invention to provide a process for producing the novel VB6PP as defined above, which comprises cultivating a microorganism belonging to the genus *Sinorhizobium* which is capable of producing the VB6PP having the above physico-chemical properties, in an aqueous nutrient medium under aerobic conditions, disrupting cells of the microorganism and isolating and purifying the VB6PP from the cell-free extract of the disrupted cells of the microorganism.

A still further object of the present invention is to provide a process for producing vitamin B$_6$ from VB6P which comprises contacting VB6P with (i) the VB6PP as defined above in the presence of $Mn^{2+}$, $Mg^{2+}$, $Co^{2+}$, $Sn^{2+}$ or $Ni^{2+}$, or (ii) a cell-free extract of said microorganism belonging to the genus *Sinorhizobium* which is capable of producing the VB6PP having the above physico-chemical properties, and in each of the cases (i) and (ii) isolating the resulting vitamin B$_6$ from the reaction mixture.

The physico-chemical properties of the purified sample of the VB6PP prepared according to the Examples hereinafter are as follows:

1) Enzyme Activity

The novel VB6PP of the present invention catalyzes hydrolysis of VB6P to vitamin B$_6$ in the presence of a divalent metal ion i.e. $Mn^{2+}$, $Mg^{2+}$, $Co^{2+}$, $Sn^{2+}$ or $Ni^{2+}$ according to the following formula:

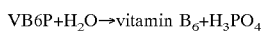

VB6P+H$_2$O→vitamin B$_6$+H$_3$PO$_4$

The standard enzyme assay was performed as follows: The basal reaction mixture of total volume 125 µl and consisting of 50 mM Tris-HCl buffer (pH 7.5), 1 mM MnCl$_2$, 1.35 µg of enzyme and water up to a total volume of 118.5 µl, and was incubated for 1 minute at 37° C. Then 6.5 µl of 800 µM PNP solution was added to give a final concentration of 40 µM, and the whole was incubated at 37° C. After incubation for 30 minutes, the reaction mixture was cooled down into an ice bath. Activity was determined in the following two ways. (i) Produced vitamin B$_6$ was microbiologically measured by the turbidity method with *Saccharomyces carlsbergensis* ATCC 9080 according to the method of Osbone and Voogt [The Analysis of Nutrients in Foods, Academic Press, London, 224–227 (1978)]. One unit of the enzyme activity was defined as the amount of enzyme synthesizing 1 µmole of vitamin B$_6$ for 30 minutes in the assay system described above. (ii) Phosphate released from putative substrates was colorimetrically measured by the malachite green method of Geladopoulos et al. [Analytical Biochemistry 192:112–116 (1991)] and this method was used for determination of substrate specificity and michaelis constant (Km) and maximum velocity (Vmax) values. The protein concentration was determined by the Lowry method [Lowry et al., J. Biol. Chem. 193:265–275 (1951)].

2) Molecular Weight

The molecular weight (hereinafter referred to as MW) of the enzyme was measured with a gel filtration column HiPrep Sephacryl S-200HR (Amersham Pharmacia Biotech (Uppsala, Sweden). The apparent MW of the enzyme was calculated to be 29,000±5,000 in comparison with the MW marker proteins: Gel filtration Standard kit, Bio-Rad Laboratories (Bio-Lad Laboratories, Richmond, Calif., USA); thyroglobulin (MW 670,000), bovine gamma globulin (MW 158,000), chicken ovalbumin (MW 44,000), equine myoglobin (MW 17,000) and vitamin B$_{12}$ (MW 1,350). SDS-Polyacrylamide gel electrophoresis (hereinafter referred to as SDS-PAGE) gave a single band with a MW of 29,000±5,000 in comparison with the molecular marker proteins: Low MW Electrophoresis calibration kit (Amersham Pharmacia Biotech, Uppsala, Sweden); bovine serum albumin (MW 67,000), ovalbumin (MW 43,000), carbonic anhydrase (MW 30,000), soybean trypsin inhibitor (MW 20,100) and α-lactalbumin (MW 14,400). This indicates that the enzyme is composed of a monomer unit. The values of the MW of the enzyme (MW 29,000±5,000) were determined as accurately as the respective methods, i.e. the gel filtration column method and the SDS-PAGE method, allowed.

3) Co-factor

The co-factor requirement of the enzyme to convert VB6P to vitamin B$_6$ was investigated. As a result, it was established that a divalent metal ion i.e. $Mn^{2+}$, $Mg^{2+}$, $Co^{2+}$, $Sn^{2+}$ or $Ni^{2+}$ could serve as a co-factor for this conversion.

TABLE 1

| Metal salts | Relative activity (%) |
|---|---|
| None | 0 |
| MnCl$_2$ | 100 |
| MgCl$_2$ | 88 |
| CoCl$_2$ | 65 |
| SnCl$_2$ | 11 |
| NiCl$_2$ | 7 |

4) Substrate Specificity

The substrate specificity of the enzyme was determined using the same method as described under 1), except for various substrate solutions (160 µM, final concentration in the reaction mixture) were used.

TABLE 2

| Substrate | Relative activity (%) |
| --- | --- |
| PNP | 100 |
| PLP | 40 |
| PMP | 0.1 |
| p-nitrophenyl phosphate | 29 |
| 1-naphthyl phosphate | 9 |
| D-glucose 6-phosphate | 0 |
| D(−)3-phosphoglyceric acid | 0 |
| 2-phosphoglycolic acid | 0 |
| adenosine triphosphate | 0 |
| adenosine diphosphate | 0 |
| adenosine monophosphate | 6 |
| O-phospho-L-serine | 0 |

5) Optimum Temperature

The enzyme activities were measured at temperatures from 5 to 45° C. The optimum temperature of the activity was 30–40° C.

TABLE 3

| Temperature (° C.) | Relative activity (%) |
| --- | --- |
| 5 | 12 |
| 10 | 21 |
| 15 | 34 |
| 20 | 49 |
| 25 | 74 |
| 30 | 91 |
| 35 | 100 |
| 40 | 89 |
| 45 | 53 |

6) Optimum pH

The correlation between the enzyme activity and the pH values of the reaction mixture was determined by using the same enzyme assay method as described under 1). The optimum pH of the enzyme reaction was found to be 7.0–8.0.

TABLE 4

| Buffer | pH | Relative Activity (%) |
| --- | --- | --- |
| Tris-maleate | 5.5 | 31 |
| ditto | 6.0 | 39 |
| ditto | 6.5 | 64 |
| ditto | 7.0 | 91 |
| ditto | 7.25 | 98 |
| ditto | 7.5 | 100 |
| Tris-HCl | 7.5 | 73 |
| ditto | 7.75 | 71 |
| ditto | 8.0 | 63 |
| ditto | 8.5 | 48 |
| ditto | 9.0 | 29 |
| ditto | 9.5 | 15 |

7) Temperature Stability

The enzyme solution was treated at various temperatures for 10 minutes, and the remaining enzyme activities were measured by using the same enzyme assay method as described under 1). It was established that the enzyme activity was decreased with increasing temperature, becoming completely inactivated at 50° C.

TABLE 5

| Temperature (° C.) | Relative activity (%) |
| --- | --- |
| 0 | 100 |
| 30 | 64 |
| 35 | 57 |
| 40 | 51 |
| 45 | 41 |
| 50 | 0.1 |
| 55 | 0 |

7) Michaelis Constant (Km) and Maximum Velocity (Vmax) Values

The Km value of the enzyme was measured by using PNP and PLP as the substrates. The basic enzyme assay method is the same as described under 1), but the substrate concentration was varied. The $K_m$ and $V_{max}$ values against PNP were 330 μM and 92 nmol/min/mg, respectively. On the other hand, the $K_m$ and $V_{max}$ values against PLP were 1.22 mM and 46 nmol/min/mg, respectively. The $K_m$ and $V_{max}$ values were calculated on the basis of the known Michaelis-Menten equation. Km is the concentration of the substrate that gives 50% of the Vmax of the enzyme reaction. The values give a useful indication of the catalytic properties of the enzyme for the involved substrate.

8) Purification Procedure

The purification of the VB6PP may in principle be effected by any combination of known purification methods, such as fractionation with precipitants, e.g. ammonium sulfate, polyethylene glycol and the like, ion exchange chromatography, adsorption chromatography, hydrophobic interaction chromatography, gel-filtration chromatography, gel electrophoresis and salting out and dialysis.

As mentioned above, the VB6PP by present invention can be prepared of the cultivating an appropriate microorganism in an aqueous nutrient medium under aerobic conditions, disrupting the microorganism and isolating and purifying the VB6PP from the cell-extract of the disrupted cells of the microorganism.

The microorganisms used for the present invention are microorganisms belonging to the genus *Sinorhizobium* which are capable of producing vitamin $B_6$ as defined hereinbefore. And the microorganisms which can be used in the present invention include *S. meliloti, S. fredii, S. xinjiangense, S. saheli, S. terangae* and. *medicae*. Mutants of said microorganism can also be used in the present invention.

A preferred strain is *Sinorhizobium meliloti*. The specific strain most preferably used in the present invention is deposited at the Institute for Fermentation, Osaka, 17–85, Juso-honmachi 2-chome, Yodogawa-ku Osaka 523–8686 Japan as *Sinorhizobium meliloti* IFO 14782, and also deposited at the DSM, Deutsche Sammlung Von Mikroorganismen und Zellkulturen GmbH, Mascheroder Weg 1b, D-3300 Braunschweig, Germany as DSM No. 10226 under the Budapest Treaty.

The microorganism may be cultured in a nutrient medium containing saccharides such as glucose and sucrose, alcohols such as ethanol and glycerol, fatty acids such as oleic acid and stearic acid, or esters thereof, or oils such as rapeseed oil and soybean oil as carbon sources; urea, ammonium sulfate, ammonium chloride, sodium nitrate, peptone, amino acids, corn steep liquor, bran, yeast extract and the like as nitrogen sources; magnesium sulfate, manganese sulfate, iron sulfate, sodium chloride, calcium carbonate, potassium monohydrogen phosphate, potassium dihydrogen phosphate and the like as inorganic salt sources; and malt extract, meat extract and the like as other nutrient sources. The pH of the culture medium may be from about 5 to 9, preferably from about 6 to about 8. The temperature range for the cultivation is suitably from about 10° C. to about 45° C., preferably from about 25° C. to about 40° C. The cultivation time is normally from about 1 to about 5 days, preferably about 1 to about 3 days. Aeration and agitation during the cultivation usually give favorable results.

An embodiment for isolation and purification of the VB6PP from the microorganism after the cultivation is as follows:

Cells are harvested from the liquid culture by centrifugation or filtration.

The harvested cells are washed with water, physiological saline or a buffer solution having an appropriate pH.

The washed cells are pretreated in a buffer containing EDTA/lysozyme and disrupted by means of a homogenizer, sonicator, French press and the like to give a solution of disrupted cells.

The VB6PP is isolated and purified from the cell-free extract of disrupted cells.

The VB6PP provided by the present invention is useful as a catalyst for the production of vitamin $B_6$ from VB6P.

The reaction of the VB6PP-catalyzed hydrolysis of VB6P to vitamin $B_6$ is conveniently conducted at pH values from about 5.5 to about 9.0 for 15 minutes to 5 hours in the presence of a divalent metal in a solvent. A more preferable pH range is from of about 6.5 to about 8.0. As a solvent, any buffer which maintains the pH in the range of about 5.5 to about 9.5 such as Tris-HCl buffer, Tris-maleate buffer, Bis-tris buffer, HEPES (Dojindo Laboratories, Kumamoto prefecture, Japan) buffer and the like, is suitable.

A preferred pH range of carrying out the reaction is from about 15° C. to about 45° C., and a more preferable temperature range is from of about 25° C. to about 40° C. The reaction usually gives the best result when the pH and the temperature are set at about 6.5 to about 8.0 and about 37° C.

The concentration of VB6P in the solvent depends on the other reaction conditions, but in general is from 1 $\mu$M to 1 M, preferably from 10 $\mu$M to 100 mM.

The amount of a divalent metal suitably present in the reaction mixture depends on the other reaction conditions, but in general is in each case independently about 1 $\mu$M to 100 mM.

In the reaction, the VB6PP may also be used in an immobilized state with an appropriate carrier. Any means of immobilizing enzymes generally known in the art may be used. For instance, the enzyme may be bound directly to a membrane, granules or the like of a resin having one or more functional groups, or it may be bound to the resin through bridging compounds having one or more functional groups, e.g. glutaraldehyde. Such enzyme immobilizing means are described for example on pages 369–394 of the $2^{nd}$ Edition of Microbial Enzymes and Biotechnology, Elsevier Applied Science (1990); Ed. Fogarty and Kelly).

The following Examples further illustrate the present invention.

EXAMPLE 1

Preparation of VB6PP

All the operations were performed at 4° C., and the buffer was 10 mM Tris-HCl buffer (pH 7.5) containing 1 mM dithiothreitol, 0.1 mM phenylmethylsulfonyl fluoride and 15% sucrose unless otherwise stated.

(1) Cultivation of *Sinorhizobium meliloti* IFO 14782 (DSM No. 10226): The microorganisms were cultured in a seed medium containing 1% glucose, 0.5% polypeptone (Nihon Pharmaceutical Co., Osaka, Japan), 0.2% yeast extract (Difco Laboratories, Detroit, Mich., USA), 0.05% $MgSO_4.7H_2O$, 0.001% $MnSO_4.5H_2O$ and 0.001% $FeSO_4.7H_2O$ at 28° C. for 17 hours. The seed culture was transferred into a 500 ml flask containing 200 ml of a fermentation medium including 4% glucose, 2% polypeptone, 0.2% yeast extract, 0.05% $MgSO_4.7H_2O$, 0.05% $MnSO_4.5H_2O$, 0.001% $FeSO_4.7H_2O$ and one drop of antifoam CA-115 (Nippon Yushi Co., Ltd., Tokyo, Japan). The flask was shaken on a flask shaker at 28° C. After cultivation for 72 hours, 59.5 g of wet cells was obtained from 3.4 liters of the culture broth by centrifugation at 10,400×g for 10 minutes.

(2) Treatment of EDTA-lysozyme: Lysozyme/EDTA treatment was performed to remove the periplasmic fraction of the cells according to the method of Glenn et al. [J. Gen. Microbiol. 112:405–409 (1979)]. The wet cells (59.5 g) were suspended in 340 ml of 30 mM Tris-HCl buffer (pH 8.0) containing 20% sucrose and 1 mM EDTA. 170 mg of lysozyme (Sigma Chemical Co., St. Louis, Mo., USA) was added to the suspension stirring at room temperature, and then the stir was continued for 20 minutes. The cells were recovered by centrifugation at 10,400×g for 10 minutes.

(3) Preparation of the cell-free extract: The cells were suspended in 340 ml of the buffer, and passed through a French pressure cell at 800 $kg/cm^2$. After the treatment, the homogenate was centrifuged at 34,000×g for 90 minutes. As a result, 280 ml of cell-free extract containing 8,570 mg of proteins was obtained.

(4) Q Sepharose HP chromatography: The cell-free extract (280 ml) obtained in the previous step was applied to a Q Sepharose HP column (44 mm in diameter and 17 cm in height; Amersham Pharmacia Biotech, Uppsala, Sweden) which was equilibrated with the buffer. After washing with the column with the same buffer, the enzyme was eluted at the concentration of 0.4 M KCl. The active fractions (350 ml) were collected and dialyzed overnight against 4 liters of the buffer.

(5) Q Sepharose HP rechromatography: The dialyzed sample (5,700 mg protein) obtained in the previous step was rechromatographed with a Q Sepharose HP column (44 mm in diameter and 12.5 cm in height) which was equilibrated the buffer. After washing with the column with the same buffer, the enzyme was eluted at the concentration of 0.25 M KCl with a linear gradient of KCl (0–0.5 M). The active fractions were collected and dialyzed overnight against 4 liters of the buffer.

(6) Ether Toyopearl chromatography: To the dialyzed enzyme solution (316 mg protein) obtained in the previous step was added ammonium sulfate to give a concentration of 1.3 M. Then the resultant sample was applied to a Ether Toyopearl column (2.5 cm in diameter and 15 cm in height; Tosoh Co., Tokyo, Japan) which was equilibrated with the buffer containing 1.3 M ammonium sulfate. After washing the buffer containing 1.3 M ammonium sulfate, the enzyme was eluted at the concentration of 0.86 M ammonium sulfate with a linear gradient of ammonium sulfate (1.3–0.5 M). The active fractions were collected.

(7) Resource ISO chromatography: To the active enzyme solution (74 mg protein) obtained in the previous step was added ammonium sulfate to give a concentration of 1.2 M.

Then the active enzyme solution was applied to a Resource ISO 6 ml column (Amersham Pharmacia Biotech, Uppsala, Sweden) which was equilibrated with the buffer containing 1.2 M ammonium sulfate. After washing the buffer with 1.2 M ammonium sulfate, the enzyme was eluted at the concentration of 0.74 M ammonium sulfate with a linear gradient of ammonium sulfate (1.2–0.5 M). The active fractions were collected and dialyzed overnight against 4 liters of the buffer.

(8) HiPrep 16/60 Sephacryl S-200HR column: The dialyzed sample from previous step was concentrated by ultrafiltration (Centriplus YM-10 and followed by Microcon YM-10 concentrators, Amicon Inc., Beverly, Mass., USA) to 300 µl. The sample (4.2 mg protein) was applied to a HiPrep 16/60 Sephacryl S-200HR column (16 mm in diameter and 60 cm in height; Amersham Pharmacia Biotech, Uppsala, Sweden) which was equilibrated by 50 mM Tris-HCl (pH 7.5) containing 15% sucrose, 1 mM DTT and 150 mM KCl. The enzyme was eluted with 70.5 ml of the buffer. This enzyme gave a homogenous band on SDS-PAGE analyses.

TABLE 6

Summary of the purification steps of the enzyme

| Step | Total activity (unit) | Total protein (mg) | Specific activity (unit/mg protein) | Yield (%) |
| --- | --- | --- | --- | --- |
| Cell-free extract | 4.1 | 8,570 | 0.00048 | 100 |
| Q sepharose (1) | 3.4 | 5,700 | 0.0006 | 83 |
| Q sepharose (2) | 2.5 | 316 | 0.0079 | 62 |
| Ether Toyopearl | 1.6 | 74 | 0.022 | 39 |
| Resource ISO | 1.2 | 4.2 | 0.29 | 28 |
| Sephacryl S-200 | 0.74 | 0.71 | 1.0 | 18 |

(9) Identification of the reaction product: The reaction mixture of total volume 5 ml consisting of 50 mM Tris-HCl buffer (pH 7.5), 640 µM PNP, 1 mM $MnCl_2$ and 108 µg of the enzyme was incubated at 37° C. After incubation for 1 hour, the reaction mixture was boiled for 3 minutes in a water bath and the resultant denaturated proteins in the reaction mixture were removed by centrifugation. The supernatant was applied on a Amberlite CG-120 (Rohm and Haas Company, Philadelphia, Pa., USA) column (16 mm in diameter and 11 cm in length). The column was washed with 40 ml of water and developed by 5% ammonium solution. Fractions eluted with the ammonium solution were pooled, concentrated under reduced pressure. The residue was dissolved in a small amount of methanol, and then analyzed on high pressure liquid chromatography under analytical conditions as follows: column, a Capcell pak $C_{18}$ SG120 column (4.6 mm in diameter and 250 mm in height, Shiseido Co., Tokyo, Japan); mobile phase, 0.1M sodium perchlorate, 0.1M potassium phosphate and 2% acetonitrile (pH 3.5); flow rate, 1 ml/minute; a UV detector set at 292 nm. As a result, the sample was identified as being pyridoxol in comparison with a standard sample of pyridoxol.

What is claimed is:

1. A purified vitamin $B_6$ phosphate-phosphatase having the following physico-chemical properties:
   a) Molecular weight: 29,000±5,000 consisting of a monomer having a molecular weight of 29,000±5,000 as determined by gel filtration and SDS-Polyacrylamide gel electrophoresis;
   b) Co-factor: $Mn^{2+}$, $Mg^{2+}$, $Co^{2+}$, $Sn^{2+}$ or $Ni^{2+}$;
   c) Substrate specificity: active on pyridoxol 5'-phosphate, pyridoxal 5'-phosphate and pyridoxamine 5'-phosphate;
   d) Optimum temperature: 30–40° C. at pH 7.5; and
   e) Optimum pH: 7.0–8.0.

2. The purified vitamin $B_6$-phosphate phosphatase according to claim 1, which is obtained from a microorganism belonging to the genus *Sinorhizobium*.

3. The purified vitamin $B_6$-phosphate phosphatase according to claim 2, wherein the microorganism is *Sinorhizobium meliloti* IFO 14782 (DSM No. 10226) or a mutant thereof, which produces the vitamin $B_6$-phosphate phosphatase.

4. A process for producing vitamin $B_6$-phosphate phosphatase which comprises cultivating a microorganism belonging to the genus *Sinorhizobium* which produces vitamin $B_6$-phosphate phosphatase having the following properties:
   a) Molecular weight: 29,000±5,000 consisting of a monomer having a molecular weight of 29,000±5,000 as determined by gel filtration and SDS-Polyacrylamide gel electrophoresis;
   b) Co-factor: $Mn^{2+}$, $Mg^{2+}$, $Co^{2+}$, $Sn^{2+}$ or $Ni^{2+}$;
   c) Substrate specificity: active on pyridoxol 5'-phosphate, pyridoxal 5'-phosphate and pyridoxamine 5'-phosphate;
   d) Optimum temperature: 30–40° C. at pH 7.5; and
   e) Optimum pH: 7.0–8.0, in an aqueous nutrient medium under aerobic conditions, disrupting the cells of the microorganism and isolating and purifying the vitamin $B_6$-phosphate phosphatase from the cell-free extract of the disrupted cells of the microorganism.

5. The process according to claim 4, wherein the microorganism is *Sinorhizobium meliloti* IFO 14782 (DSM No. 10226) or a mutant thereof, which produces the vitamin $B_6$-phosphate phosphatase.

6. The process according to claim 4, wherein the cultivation is effected in a pH range from 5.0 to 9.0, and in a temperature range from 10° C. to 45° C. for 1 day to 5 days.

7. The process according to claim 4, wherein the cultivation is effected in a pH range from 6.0 to 8.0, and in a temperature range from 25° C. to 40° C. for 1 day to 3 days.

8. A process for producing vitamin $B_6$ from vitamin $B_6$ phosphate which comprises contacting vitamin $B_6$ phosphate with a vitamin $B_6$-phosphate phosphatase having the following properties:
   a) Molecular weight: 29,000±5,000 consisting of a monomer having a molecular weight of 29,000±5,000 as determined by gel filtration and SDS-Polyacrylamide gel electrophoresis;
   b) Co-factor: $Mn^{2+}$, $Mg^{2+}$, $Co^{2+}$, $Sn^{2+}$ or $Ni^{2+}$;
   c) Substrate specificity: active on pyridoxol 5'-phosphate, pyridoxal 5'-phosphate and pyridoxamine 5'-phosphate;
   d) Optimum temperature: 30–40° C. at pH 7.5; and
   e) Optimum pH: 7.0–8.0.

in the presence of and isolating the $Mn^{2+}$, $Mg^{2+}$, $Co^{2+}$, $Sn^{2+}$ or $Ni^{2+}$; and isolating the resulting vitamin $B_6$ from the reaction mixture.

9. The process according to claim 8, wherein the vitamin $B_6$-phosphate phosphatase is obtained from *Sinorhizobium meliloti* IFO 14782 (DSM No. 10226) or its mutant, which produces the vitamin $B_6$-phosphate phosphatase.

10. The process according to claim 8, wherein the contacting is effected in a pH range from 5.5 to 9.0, and in a temperature range from 15° C. to 45° C. for 15 minutes to 5 hours.

11. The process according to claim 8, wherein the contacting is effected in a pH range from 6.5 to 8.0, and in a temperature range from 25° C. to 40° C. for 30 minutes to 3 hours.

12. A process for producing vitamin $B_6$ from vitamin $B_6$ phosphate which comprises contacting vitamin $B_6$ phosphate with a cell-free extract of a microorganism belonging to the genus *Sinorhizobium* which produces a vitamin $B_6$-phosphate phosphatase with the following properties:
   a) Molecular weight: 29,000±5,000 consisting of a monomer having a molecular weight of 29,000±5,000 as determined by gel filtration and SDS-Polyacrylamide gel electrophoresis;
   b) Co-factor: $Mn^{2+}$, $Mg^{2+}$, $Co^{2+}$, $Sn^{2+}$ or $Ni^{2+}$;
   c) Substrate specificity: active on pyridoxol 5'-phosphate, pyridoxal 5'-phosphate and pyridoxamine 5'-phosphate;
   d) Optimum temperature: 30–40° C. at pH 7.5; and
   e) Optimum pH: 7.0–8.0.
   and isolating the resulting vitamin $B_6$ from the reaction mixture.

13. The process according to claim 12, wherein the microorganism is *Sinorhizobium meliloti* IFO 14782 (DSM No. 10226) or a mutant thereof, which produces the vitamin $B_6$-phosphate phosphatase.

14. The process according to claim 12, wherein the contacting is effected in a pH range from 5.5 to 9.0, and in a temperature range from 15° C. to 45° C. for 15 minutes to 5 hours.

15. The process according to claim 12, wherein the contacting is effected in a pH range from 6.5 to 8.0, and in a temperature range from 25° C. to 40° C. for 30 minutes to 3 hours.

16. The process according to claim 9, wherein the contacting is effected in a pH range from 5.5 to 9.0, and in a temperature range from 15° C. to 45° C. for 15 minutes to 5 hours.

17. The process according to claim 9, wherein the contacting is effected in a pH range from 6.5 to 8.0, and in a temperature range from 25° C. to 40° C. for 30 minutes to 3 hours.

18. The process according to claim 10, wherein the contacting is effected in a pH range from 6.5 to 8.0, and in a temperature range from 25° C. to 40° C. for 30 minutes to 3 hours.

19. The process according to claim 16, wherein the contacting is effected in a pH range from 6.5 to 8.0, and in a temperature range from 25° C. to 40° C. for 30 minutes to 3 hours.

* * * * *